(12) United States Patent
Young et al.

(10) Patent No.: US 6,656,161 B2
(45) Date of Patent: Dec. 2, 2003

(54) MAGNIFYING HUB

(75) Inventors: Christopher S. Young, South Kent, CT (US); Loretta Luhman, Litchfield, CT (US)

(73) Assignee: ISPG, Inc., New Milford, CT (US)

( * ) Notice: Subject to any disclaimer, the term of this patent is extended or adjusted under 35 U.S.C. 154(b) by 73 days.

(21) Appl. No.: 09/951,014

(22) Filed: Sep. 12, 2001

(65) Prior Publication Data

US 2002/0055715 A1 May 9, 2002

Related U.S. Application Data

(60) Provisional application No. 60/246,776, filed on Nov. 8, 2000.

(51) Int. Cl.$^7$ ............................................. A61M 5/178
(52) U.S. Cl. .................... 604/168.01; 604/900; 604/584
(58) Field of Search ................. 604/48, 93.01, 604/158, 164.01, 168.01, 181, 187, 264, 272, 523, 533–535, 537, 900, 905; 600/573, 576–584

(56) References Cited

U.S. PATENT DOCUMENTS

| | | | |
|---|---|---|---|
| 4,384,581 A | 5/1983 | Conway | |
| 4,475,915 A | 10/1984 | Sloane | |
| 4,654,031 A | 3/1987 | Lentz | |
| 4,713,061 A | 12/1987 | Tarello et al. | |
| 5,030,207 A | 7/1991 | Mersch et al. | |
| 5,137,518 A | 8/1992 | Mersch | |
| 5,701,910 A | * | 12/1997 | Powles et al. ............... 600/577 |
| 2002/0099335 A1 | * | 7/2002 | Zohmann .................... 604/198 |

FOREIGN PATENT DOCUMENTS

EP         0139872 A1    8/1985

* cited by examiner

*Primary Examiner*—LoAn H. Thanh
(74) *Attorney, Agent, or Firm*—Carmody & Torrance LLP

(57) ABSTRACT

An arrangement used in connection with the withdrawal of cerebral spinal fluid (CSF) from a spinal column comprising a hub having a chamber therein for receiving CSF; a cannula being coupled to the hub to permit communication of CSF with the hub, the cannula having a first end securable within the hub and a second end dimensioned to permit withdrawal of CSF from a spinal column; wherein the hub includes walls forming an opening therebetween, and wherein a arcuately shaped magnifier is disposed within the opening, wherein the magnifier includes edges that extend below the top surface of the walls of the hub such that at least a portion of the curved outer surface of the magnifier extends below the top surface of the walls of the hub; whereby the magnifier can be positioned in close proximity to the chamber to improve magnification of the CSF as it enters the chamber and decrease the recognition time from when the CSF first enters the chamber of the hub. A flashback indicator and a hub for use in a flashback arrangement are also provided.

11 Claims, 3 Drawing Sheets

MAGNIFYING HUB

RELATED APPLICATIONS

This application claims the benefit of U.S. Provisional Application No. 60/246,776, filed Nov. 8, 2000.

BACKGROUND OF THE INVENTION

Spinal needles are primarily used to introduce chemicals into, withdraw CSF (cerebral spinal fluid) from, and measure the pressure in the spinal column. Combined spinal-epidural techniques are also prevalent using a needle through needle technique to guide an epidural needle almost as far as the dura mater, then advance the spinal needle into the dura itself. Spinal needles are also used to introduce chemicals into other areas of the body near various nerve endings. Standard procedure entails placing an introducer needle through one of the lumbar spine interspaces, then advancing a spinal needle through the introducer through the ligamentum flavum and the arachnoid. Once the dura mater is reached, CSF appears in the hub, serving as an indication that the spinal needle has been properly placed.

Prior art devices that indicate the flashback of fluids such as blood, are well known. Additionally, at least one flashback indicator system, described in European Patent Application No. 139,872, describes the use of a magnifier element for providing an apparent enhanced visual image of the flashback of the blood as it flows into the hub.

However, the aforementioned devices are perceived to be deficient in several respects. For example, it is a perceived deficiency that the current devices do not sufficiently enhance the flashback of the liquid, such as blood or CSF. By using the invention disclosed herein, the practitioner can more readily determine that proper needle placement has been made than previously achievable.

Additionally, since the amount of CSF fluid lost through the needle is necessarily small to prevent spinal headache, and in order for practitioners to quickly visualize this fluid, needle manufactures have attempted to modify standard needle hubs by reducing the volume inside the hub, protruding the cannula directly into the hub viewing area, and allowing the fluid to be easily viewed by reducing the amount of plastic between the hub inside diameter and the viewer. However, even these constructions have perceived drawbacks some of which are set forth below, and some of which will become apparent after a review of the following disclosure.

Accordingly, because of the need to quickly view the CSF fluid or other fluid, such as blood, it is desired to provide a hub especially designed to rapidly show the fluid by magnifying it, preferably about three (3) times, to the practitioner as soon as it appears from the cannula. The present invention achieves these and other objectives by providing a cylindrical optical magnifier molded directly as a part of the plastic hub in a manner that more quickly and efficiently allows the practitioner to know when the dura mater, or other lining, such as in a blood vessel, has been punctured.

SUMMARY AND OBJECTS OF THE INVENTION

Therefore, it is an object of the present invention to provide an improved magnifying hub.

It is another object of the present invention to provide an improved cylindrical CSF magnifier molded directly as a part of a spinal needle hub to magnify CSF fluid, preferably about three (3) times size.

It is another object of the invention to frost particular surfaces of the hub in order to improve the contrast between the magnifier and the hub surfaces to thus facilitate the viewing of the contents of the flashback chamber of the hub.

It is yet another object of the present invention to coordinate the shape of the magnifier and the internal flashback chamber to further reduce or eliminate any distortion of the contents of the chamber.

It is still another object to provide an improved magnifier hub that can be easily manufactured.

It is another object of the present invention to reduce or eliminate distortion of the magnified fluid, achievable by coordinating the shape of the flashback chamber and the magnifier.

It is yet another object of the present invention to provide a magnifying hub that achieves all of the foregoing and below-mentioned objectives and advantages while remaining sufficiently small in size.

Still other objects and advantages of the invention will in part be obvious and will in part be apparent from the specification.

The invention accordingly comprises the features of construction, combination of elements and arrangement of parts that will be exemplified in the disclosure hereinafter set forth, and the scope of the invention will be indicated in the claims.

Generally speaking, the present invention comprises an arrangement used in connection with the withdrawal of cerebral spinal fluid (CSF) from a spinal column. In a preferred embodiment, the arrangement comprises a hub having a chamber therein for receiving CSF, a cannula coupled to the hub to permit communication of CSF with the hub and dimensioned to permit withdrawal of the CSF from a spinal column, wherein the hub includes walls forming an opening therebetween, and wherein a arcuately shaped magnifier is disposed within the opening. The magnifier preferably includes edges that extend below the top surface of the walls of the hub such that at least a portion of the curved outer surface of the magnifier extends below the top surface of the walls of the hub so as to allow the magnifier to be positioned in close proximity to the chamber to improve magnification of the CSF as it enters the chamber and decrease the recognition time from when the CSF first enters the chamber of the hub.

In yet a preferred construction, the top surface of at least one of the walls around the opening in which the magnifier is disposed is frosted to increase the contrast between the magnified area and the hub. Further the magnifier is preferably dimensioned to magnify the CSF fluid about three (3) times. The hub may include finger grips located on adjacent sides of the hub for facilitating the positioning of the hub during cannula placement in a spinal column. An integrally molded bevel orientation indicator may be provided on the cannula hub for facilitating the proper alignment of the cannula.

Preferably, a portion of the curved outer surface of the magnifier extends above the top surface of the walls of the hub on the side of the hub through which the opening is formed to both improve magnification while maintaining the small size of the hub. Further, both the magnifier and the chamber of the hub are cylindrical in shape to eliminate or reduce magnification distortion.

In accordance with the present invention, a flashback indicator is also provided wherein the chamber therein is dimensioned to receiving a bodily fluid, such as blood or CSF. Similarly, the cannula is coupled to the hub to permit communication of the bodily fluid with the hub. Likewise, the hub includes walls forming an opening therebetween for the positioning of an arcuately shaped magnifier to be disposed therein. The magnifier includes edges that extend below the top surface of the walls of the hub such that at least a portion of the curved outer surface of the magnifier extends below the top surface of the walls of the hub to permit the magnifier to be positioned in close proximity to the chamber to improve magnification of the bodily fluid as it enters the chamber and decrease the recognition time from when the bodily fluid first enters the chamber of the hub.

The present invention also discloses and claims a hub for use in such a flashback arrangement.

BRIEF DESCRIPTION OF THE DRAWINGS

For a fuller understanding of the invention, reference is made to the following description taken in connection with the accompanying drawings, in which.

Identically labeled elements appearing in different ones of the above-described figures refer to the same elements but may not be referenced in the description for all figures.

DETAILED DESCRIPTION OF THE PREFERRED EMBODIMENT

Generally speaking, the present invention provides many advantages over the prior art. Specifically, not only does the present invention overcome the above-mentioned drawbacks, but the present invention achieves the following objectives and advantages, namely, a cylindrical molding of the magnifier permits magnified viewing directly into hub of the CSF or other fluid, preferably about three (3) times size; a bevel orientation arrow allows the practitioner to feel for correct bevel alignment under low light conditions; a frosted area surrounding the magnifier improves highlighting of the magnified area; finger grips on the hub's edges improves better positioning of the hub; providing a butt end of the hub to be viewable through the magnifier improves visualization among other advantages set forth below and inherent therein; providing a cannula that protrudes directly into hub cavity allows for quick visualization of fluid; a small volume internal diameter ("I.D.") of the hub's interior permits pooling of fluid for quick visualization; a coordination of the shape of the magnifier and flashback chamber reduces or eliminates distortion of the fluid being magnified, and the positioning of the magnifier below and above the side walls of the hub as disclosed herein allows for increased magnification while reducing the hub's overall size.

Figure 1:
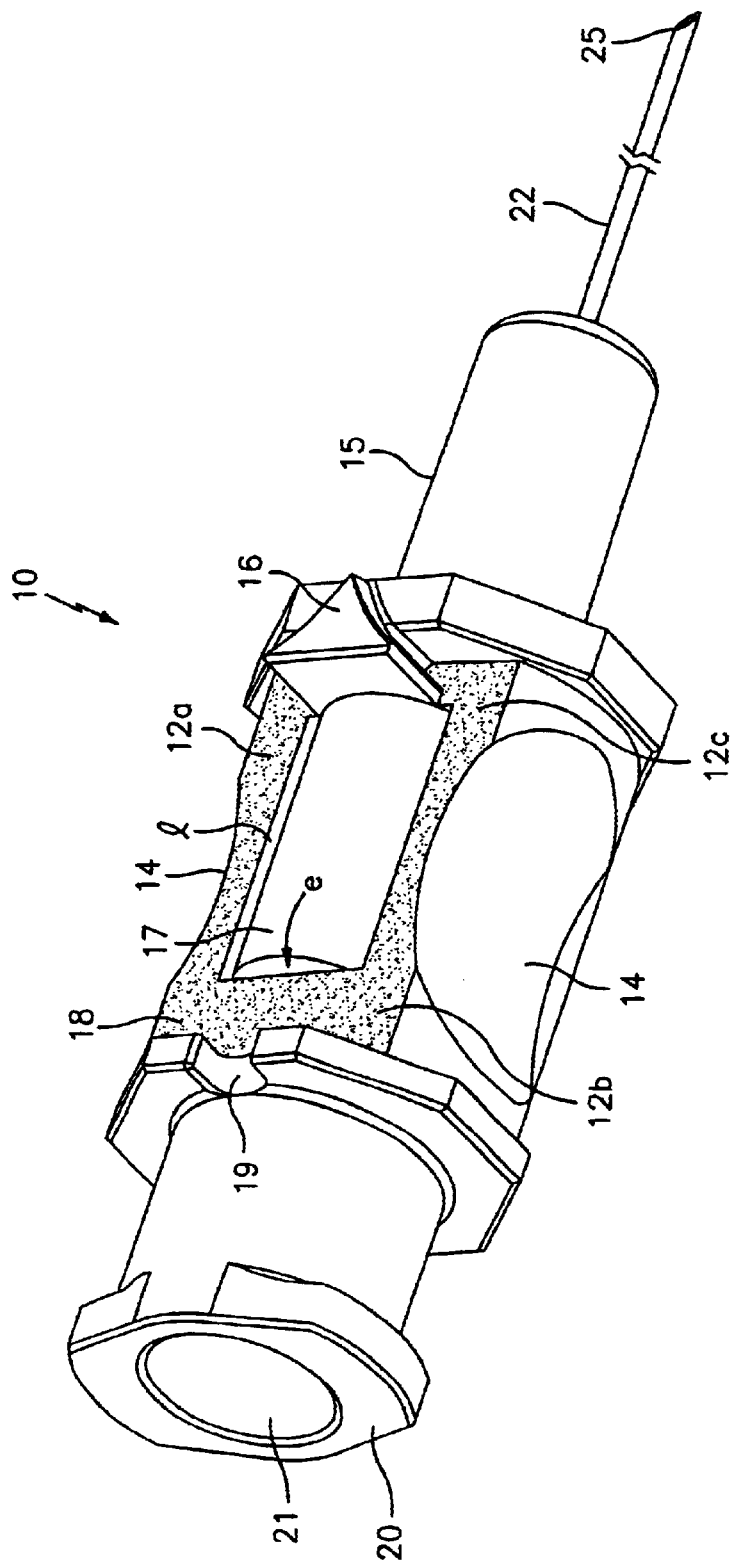
FIG. 1 is a perspective view of a magnifying hub constructed in accordance with the present invention.
Figure 2:
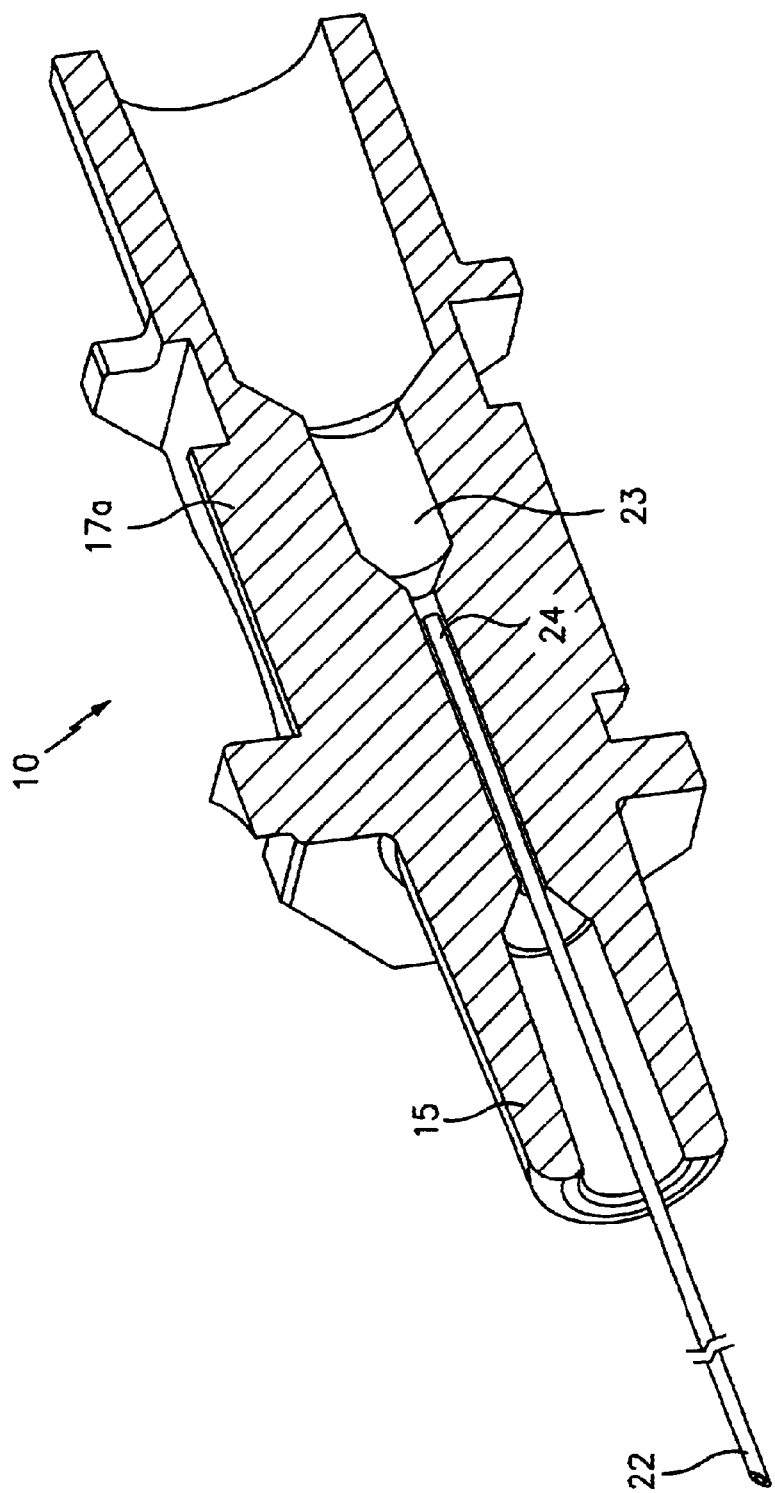
FIG. 2 is a cross-sectional view of the magnifying hub of FIG. 1 more particularly highlighting certain aspects of the present invention.

To achieve the foregoing, reference is now made to FIGS. 1 and 2 for a more detailed description of the preferred construction of the present invention. In particular, FIG. 1 illustrates a perspective external view of a magnifying hub, generally indicated at 10, constructed in accordance with the present invention.

Magnifying hub 10 may be utilized in a flashback arrangement, wherein the flashback arrangement comprises the hub and a cannula 22 coupled to magnifying hub 10 to permit communication of a bodily fluid (i.e. CSF or blood) with magnifying hub 10. Cannula 22 has a first end 24 securable within magnifying hub 10 and a second end 25 dimensioned to permit withdrawal of the bodily fluid from a body. Cannula 22 is preferably made of stainless steel and has a pointed, beveled or conically shaped end with a side port entry. Cannula 22 may be affixed to the hub via either medical grade epoxy or insert molding to meet the pull test requirements of ISO 594.

In the preferred embodiment, magnifying hub 10 comprises a chamber 23 dimensioned to receiving the bodily fluid. On at least one side of the body of the hub 10, walls 12a,b,c are provided and an opening is formed therebetween. This opening coordinates to overly chamber 23 and, if desired, end 24 of cannula 22. An arcuately shaped magnifier 17 is disposed within the opening in a manner such that the edges of magnifier 17 extend below the top surface of walls 12a,b,c of hub 10 such that at least a portion of the curved outer surface of magnifier 17 extends below the top surface of walls 12a,b,c of hub 10. This is clearly depicted in FIGS. 1 and 3 wherein a length "1" of side wall 12a can be seen between the edge of magnifier 17 and the top surface of wall 12a. The edge of magnifier 17 also extends below the surface of wall 12c but cannot be seen in FIG. 1. In this way, magnifier 17 can be positioned in close proximity to chamber 23 to improve magnification of the bodily fluid as it enters chamber 23 and decrease the recognition time from when the bodily fluid first enters chamber 23. Magnifying hub 10 is preferably used in connection with the withdrawal of cerebral spinal fluid (CSF) from a spinal column.

The top surfaces of walls 12a,b,c, which form the opening through which magnifier 17 is positioned, are preferably frosted to increase the contrast between the magnified area and hub 10 itself.

The two side surfaces 14 of hub 10 may be concave in shape so as to provide increased finger grip for easy hub positioning during needle placement. A luer taper 15 may also be provided as an added feature of a proximal 6% luer taper allowing cannula 22 needle to be affixed onto the distal end of another needle (not shown), creating a stackable hub. An upwardly protruding molded arrow 16, which can be felt or viewed during use, is preferably molded directly into hub 10 for allowing for easy bevel cannula orientation under low light conditions.

As stated above, magnifier 17 is preferably cylindrically shaped, thus allowing CSF, or other fluid such as blood, to appear in hub 10 to be viewed at preferably about three (3) times size. The cylindrical nature of magnifier 17 extending below the surface of the walls 12a,b,c of hub 10 at the edges thereof advantageously permits the magnifier to extend closer to the internal diameter of the hub, improving magnification. Similarly, the extension below the surface as set forth permits the outer radius of magnifier 17 to extend above the surface (see arrow "e" to illustrate how outer radius of magnifier is extending above wall 12b surface) also as shown in FIG. 1, thus still further improving the magnification advantages while maintaining the device within tolerable size limits. That is, submerging the magnifier 17 below the top surface of the hub's walls 12a,b,c permits the magnifier 17 to be convexly shaped while not becoming too bulky.

The advantageous nature of the frosted surface 18 can be appreciated as magnifier 17 viewing area is offset (or contrasted) by the flat frosted area, thus allowing the magnified area to visually pop out to the practitioner as he or she is looking for CSF or other fluid and/or determining correct needle placement. A notch 19 may be provided for a stylet handle (not shown) to be locked into position during needle placement. Stylets are used to prevent coring or unintended fluid entry during needle placement. They are retracted once correct needle placement is made. A luer lock 20 is provided and is molded to ISO 594/2 dimensions allowing a syringe (not shown) to be locked into position for chemical (usually anesthetic) delivery. An orifice 21 allows entry into the cavity of hub 10 at the distal end thereof all in accordance with known technology.

Figure 3:
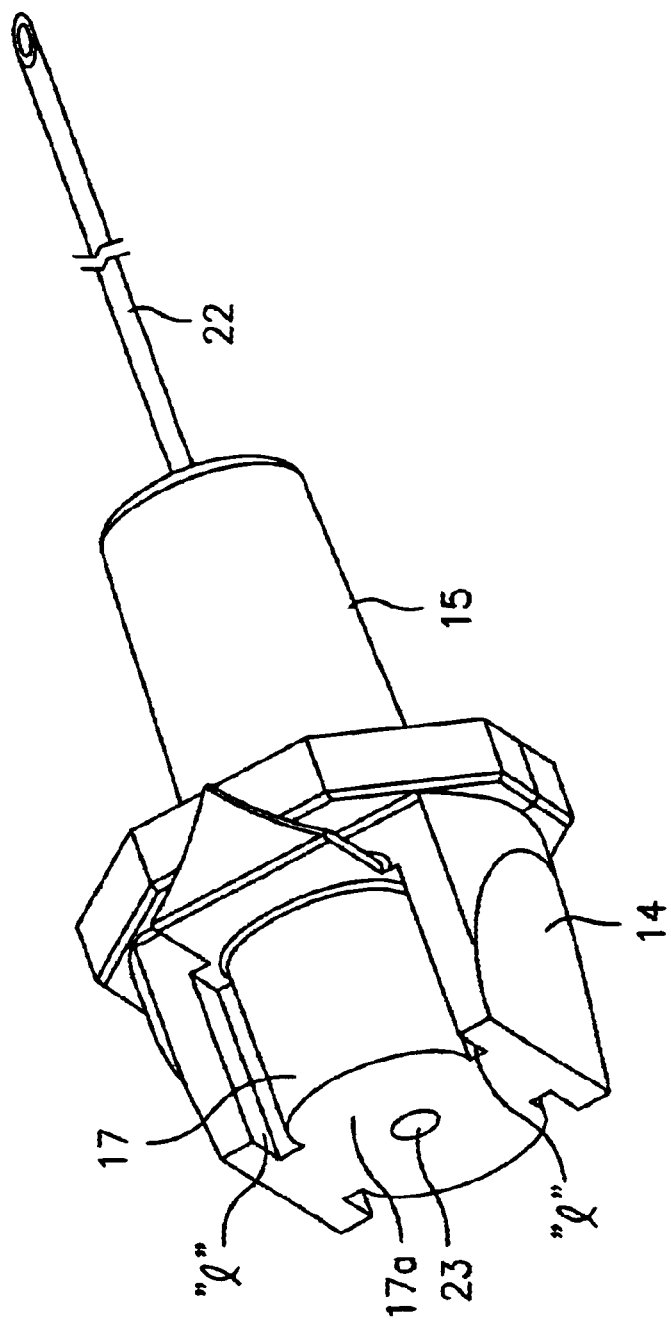
FIG. 3 is another cross sectional view of the magnifying hub of FIG. 1 particularly highlighting other aspects of the present invention.

Reference is now made specifically to FIGS. 2 and 3 which show cross-sectional views of magnifying hub 10, wherein reference number 17a indicates a cross sectional view of the magnifier, while reference number 23 indicates the flashback chamber and highlights the small volume internal diameter (ID) thereof. Magnifier 17 provides for an increased rapid visualization of the pooling of the fluid therein. As illustrated, the butt end 24 of cannula 22 may also extend into chamber 23 so as to also be magnified.

For clarity, one of the important and many distinguishing features of the present invention from known prior art is the combination of a cylindrical CSF magnifier molded directly as a part of a spinal needle hub to magnify CSF fluid, preferably about three (3) times size. The feature of a frosted surface to contrast the magnifier is also believed to be novel and unobvious feature. Lastly the coordinated shape (i.e. cylindrical in the preferred embodiment) of chamber 23 and the magnifier 17 reduces or eliminates any distortion of the contents of the chamber, and is a desired advantage for this reason. Preferably, magnifying hub 10 may be integrally molded from medical grade clear plastic.

It can thus be seen that a magnifying hub (or hub and cannula arrangement) constructed in accordance with the preferred embodiment set forth above is an improvement over state of the art devices. For example, by providing a magnifier that is dimensioned to magnify fluid, such as CSF, about three (3) times, a practitioner's can more precisely and quickly determine when the spinal column has been penetrated. By providing finger grips as set forth above, the positioning of the hub during cannula placement in a spinal column can be facilitated. If the end of the cannula is beveled, as end 25 in the preferred embodiment preferably is, an integrally molded bevel orientation indicator on the cannula hub may facilitate the proper alignment of the cannula. By providing a portion of the curved outer surface of the magnifier below and above the top surface of the walls of the hub on the side of the hub through which the opening is formed, an increased magnifying ability while maintaining the hub's small size is provided. Lastly, by coordinating the shape of the magnifier with the shape of the chamber reduces or eliminates any visual distortion of the contents (i.e. fluid) of the chamber.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

While the invention has been particularly shown and described with respect to preferred embodiments therof,it will be understood by those skilled in the art that changes in form and details may be made therein without departing from the scope and spirit of the invention.

What is claimed is:

1. An arrangement used in connection with the withdrawal of cerebral spinal fluid (CSF) from a spinal column, the arrangement comprising:
   a hub having a chamber therein for receiving CSF;
   a cannula, the cannula being coupled to the hub to permit communication of CSF with the hub, the cannula having a first end securable within the hub and a second end dimensioned to permit withdrawal of CSF from a spinal column;
   wherein the hub includes walls forming an opening therebetween, and wherein a arcuately shaped magnifier is disposed within the opening, wherein the magnifier includes edges that extend below the top surface of the walls of the hub such that at least a portion of the curved outer surface of the magnifier extends below the top surface of the walls of the hub;
   whereby the magnifier can be positioned in close proximity to the chamber to improve magnification of the CSF as it enters the chamber and decrease the recognition time from when the CSF first enters the chamber of the hub.

2. The arrangement as claimed in claim 1, wherein the second end of the cannula is beveled.

3. The arrangement as claimed in claim 2, including an integrally molded bevel orientation indicator on the cannula hub for facilitating the proper alignment of the cannula.

4. The arrangement as claimed in claim 1, where the top surface of at least one of the walls around the opening in which the magnifier is disposed is frosted to increase the contrast between the magnified area and the hub.

5. The arrangement as claimed in claim 1, wherein the magnifier is dimensioned to magnify the CSF fluid about three (3) times.

6. The arrangement as claimed in claim 1, wherein the hub includes finger grips located on adjacent sides of the hub for facilitating the positioning of the hub during cannula placement in a spinal column.

7. The arrangement as claimed in claim 1, wherein a portion of the curved outer surface of the magnifier extends above the top surface of the walls of the hub on the side of the hub through which the opening is formed.

8. The arrangement as claimed in claim 1, where the magnifier is cylindrical in shape.

9. The arrangement as claimed in claim 1, wherein the shape of the magnifier and the shape of the chamber are similar in shape to reduce or eliminate distortion of the contents of the chamber.

10. A flashback indicator comprising:
    a hub having a chamber therein dimensioned to receiving a bodily fluid;
    a cannula, the cannula being coupled to the hub to permit communication of the bodily fluid with the hub, the cannula having a first end securable within the hub and a second end dimensioned to permit withdrawal of the bodily fluid from a body;
    wherein the hub includes walls forming an opening therebetween, and wherein a arcuately shaped magnifier is disposed within the opening, wherein the magnifier includes edges that extend below the top surface of the walls of the hub such that at least a portion of the curved outer surface of the magnifier extends below the top surface of the walls of the hub;
    whereby the magnifier can be positioned in close proximity to the chamber to improve magnification of the bodily fluid as it enters the chamber and decrease the recognition time from when the bodily fluid first enters the chamber of the hub.

11. A hub for use in a flashback arrangement, wherein the flashback arrangement comprises a cannula coupleable to the hub to permit communication of a bodily fluid with the hub, the cannula having a first end securable within the hub and a second end dimensioned to permit withdrawal of the bodily fluid from a body, the hub comprising:

a chamber therein dimensioned to receiving a bodily fluid;

walls on one side of the hub forming an opening therebetween; and an arcuately shaped magnifier disposed within the opening, wherein the magnifier includes edges that extend below the top surface of the walls of the hub such that at least a portion of the curved outer surface of the magnifier extends below the top surface of the walls of the hub;

whereby the magnifier can be positioned in close proximity to the chamber to improve magnification of the bodily fluid as it enters the chamber and decrease the recognition time from when the bodily fluid first enters the chamber of the hub.

* * * * *